United States Patent
Robinson (10) Patent No.: US 9,089,714 B2
(45) Date of Patent: Jul. 28, 2015

(54) STITCHED COMPONENTS OF AN ACTIVE IMPLANTABLE MEDICAL DEVICE

(75) Inventor: David Robinson, Eveleigh (AU)

(73) Assignee: SALUDA MEDICAL PTY LIMITED, Eveleigh, NSW (AU)

( * ) Notice: Subject to any disclaimer, the term of this patent is extended or adjusted under 35 U.S.C. 154(b) by 487 days.

(21) Appl. No.: 12/549,831

(22) Filed: Aug. 28, 2009

(65) Prior Publication Data

US 2010/0262214 A1    Oct. 14, 2010

(30) Foreign Application Priority Data

Apr. 8, 2009    (AU) ................................ 2009901533

(51) Int. Cl.
*A61N 1/05*    (2006.01)
*A61N 1/375*    (2006.01)
*H05K 3/10*    (2006.01)
*A61N 1/36*    (2006.01)
*A61N 1/372*    (2006.01)

(52) U.S. Cl.
CPC .............. *A61N 1/375* (2013.01); *A61N 1/0551* (2013.01); *H05K 3/103* (2013.01); *A61B 2562/125* (2013.01); *A61N 1/3605* (2013.01); *A61N 1/37229* (2013.01); *H05K 2201/0129* (2013.01); *H05K 2201/0281* (2013.01); *H05K 2201/0308* (2013.01); *H05K 2201/10287* (2013.01); *H05K 2201/10598* (2013.01); *H05K 2203/1189* (2013.01); *Y10T 29/4913* (2015.01)

(58) Field of Classification Search
USPC ................................ 607/2, 129; 128/798, 785
See application file for complete search history.

(56) References Cited

U.S. PATENT DOCUMENTS

| | | | | |
|---|---|---|---|---|
| 2,412,201 A | * | 12/1946 | Brennan | 29/25.03 |
| 4,239,046 A | * | 12/1980 | Ong | 600/391 |
| 4,270,549 A | * | 6/1981 | Heilman | 607/129 |
| 4,475,141 A | | 10/1984 | Antonevich | |
| 4,620,550 A | * | 11/1986 | Doroshuk | 607/126 |
| 5,720,099 A | | 2/1998 | Parker et al. | |
| 6,210,771 B1 | * | 4/2001 | Post et al. | 428/100 |
| 6,421,569 B1 | | 7/2002 | Treaba et al. | |
| 7,025,596 B2 | * | 4/2006 | Zollo et al. | 439/37 |
| 2003/0040785 A1 | * | 2/2003 | Maschino et al. | 607/118 |
| 2003/0212319 A1 | * | 11/2003 | Magill | 600/382 |
| 2005/0102010 A1 | * | 5/2005 | Lau et al. | 607/129 |
| 2006/0213767 A1 | * | 9/2006 | Anaf | 204/268 |
| 2007/0251082 A1 | | 11/2007 | Milojevic et al. | |
| 2011/0132040 A1 | * | 6/2011 | Jahn et al. | 66/202 |

FOREIGN PATENT DOCUMENTS

WO    02/087471    11/2002
WO    2008/069511    6/2008

OTHER PUBLICATIONS

International Search Report, PCT/US2009/055402, completion date Nov. 4, 2009; 4 pgs.

* cited by examiner

*Primary Examiner* — Paula J Stice (57) ABSTRACT

An active implantable medical device (AIMD) comprising an implantable electronics module and a tissue interface. At least one of the electronics module and the tissue interface comprises an electrically non-conductive, biocompatible and needle-piercable base having one or more biocompatible electrically conductive strands of conductive filaments stitched to the base. As used herein, stitching a conductive filament to a base refers to sewing, embroidering or otherwise securing the filament to the base through the use of hand or machine needlework.

25 Claims, 12 Drawing Sheets

STITCHED COMPONENTS OF AN ACTIVE IMPLANTABLE MEDICAL DEVICE

CROSS-REFERENCE TO RELATED APPLICATION

The present application claims priority from Australian Provisional Patent Application No. 2009901533, filed Apr. 8, 2009, which is hereby incorporated by reference herein.

The present application is related to commonly owned and co-pending U.S. patent application Ser. No. 12/549,899 now U.S. Pat. No. 8,923,984 entitled "Knitted Electrode Assembly For An Active Implantable Medical Device," filed Aug. 28, 2009, U.S. patent application Ser. No. 12/549,457 now U.S. Pat. No. 8,897,888 entitled "Knitted Electrode Assembly And Integrated Connector For An Active Implantable Medical Device," filed Aug. 28, 2009, U.S. patent application Ser. No. 12/549,801 entitled "Knitted Catheter," filed Aug. 28, 2009 now abandoned, U.S. patent application Ser. No. 12/549,875 entitled "Bonded Hermetic Feed Through For An Active Implantable Medical Device," filed Aug. 28, 2009 now abandoned, and U.S. patent application Ser. No. 12/549,786 entitled "Electronics Package For An Active Implantable Medical Device," filed Aug. 28, 2009, which are hereby incorporated by reference herein.

BACKGROUND

1. Field of the Invention

The present invention relates generally to active implantable medical devices (AIMDs), and more particularly, to stitched components of an AIMD.

2. Related Art

Medical devices having one or more active implantable components, generally referred to herein as active implantable medical devices (AIMDs), have provided a wide range of therapeutic benefits to patients over recent decades. AIMDs often include an implantable, hermetically sealed electronics module, and a device that interfaces with a patient's tissue, sometimes referred to as a tissue interface. The tissue interface may include, for example, one or more instruments, apparatus, sensors or other functional components that are permanently or temporarily implanted in a patient. The tissue interface is used to, for example, diagnose, monitor, and/or treat a disease or injury, or to modify a patient's anatomy or physiological process.

In particular applications, an AIMD tissue interface includes one or more conductive electrical contacts, referred to as electrodes, which deliver electrical stimulation signals to, or receive signals from, a patient's tissue. The electrodes are typically disposed in a biocompatible electrically non-conductive member, and are electrically connected to the electronics module. The electrodes and the non-conductive member are collectively referred to herein as an electrode assembly.

SUMMARY

In accordance with one aspect of the present invention, a method of manufacturing an active implantable medical device (AIMD) is provided. The method comprises: providing a biocompatible, electrically non-conductive and needle-piercable base; attaching first and second components to the non-conductive base; electrically connecting the first and second components with a biocompatible, electrically conductive filament; and stitching the conductive filament to the non-conductive base.

In accordance with another aspect of the present invention, a method of manufacturing an active implantable medical device (AIMD) is provided. The method comprises: providing a biocompatible, electrically non-conductive and needle-piercable base; attaching at least one active component to the non-conductive base; attaching a biocompatible electrically conductive filament to the at least one active component; and stitching the conductive filament to the base in a pattern usable by the at least one active component to at least one of transmit and receive signals.

In accordance with a still other aspect of the present invention, an active implantable medical device (AIMD) is provided. The AIMD comprises: a biocompatible, electrically non-conductive and needle-piercable base; first and second components attached to the non-conductive base; and a biocompatible, electrically conductive filament stitched to the non-conductive base electrically connecting the first and second components.

In accordance with another aspect of the present invention, an active implantable medical device (AIMD) is provided. The AIMD comprises: a biocompatible, electrically non-conductive and needle-piercable base; at least one active component attached to the non-conductive base; and a biocompatible, electrically conductive filament attached to the at least one active component and stitched to the base in a pattern usable by the at least one active component to at least one of transmit and receive signals.

BRIEF DESCRIPTION OF THE DRAWINGS

Aspects and embodiments of the present invention are described herein with reference to the accompanying drawings, in which.

DETAILED DESCRIPTION

Aspects of the present invention are generally directed to an active implantable medical device (AIMD) comprising an implantable electronics module and a tissue interface. At least one of the electronics module and the tissue interface comprises an electrically non-conductive, biocompatible and needle-piercable base having one or more biocompatible electrically conductive strands of yarn, wire, thread, metal coated fiber or filament (generally and collectively referred to as "conductive filaments" herein) stitched to the base. As used herein, stitching a conductive filament to a base refers to sewing, embroidering or otherwise securing the filament to the base through the use of hand or machine needlework.

Embodiments of the present invention are described herein primarily in connection with one type of AIMD, a neurostimulator, and more specifically a deep brain stimulator or spinal cord stimulator. Deep brain stimulators are a particular type of AIMD that deliver electrical stimulation to a patient's brain, while spinal cord stimulators deliver electrical stimulation to a patient's spinal column. As used herein, deep brain stimulators and spinal cord stimulators refer to devices that deliver electrical stimulation alone or in combination with other types of stimulation. It should be appreciated that embodiments of the present invention may be implemented in any brain stimulator (deep brain stimulators, cortical stimulators, etc.), spinal cord stimulator or other neurostimulator now known or later developed, such as cardiac pacemakers/defibrillators, functional electrical stimulators (FES), pain stimulators, etc. Embodiments of the present invention may also be implemented in AIMDs that are implanted for a relatively short period of time to address acute conditions, as well in AIMDs that are implanted for a relatively long period of time to address chronic conditions.

Figure 1:
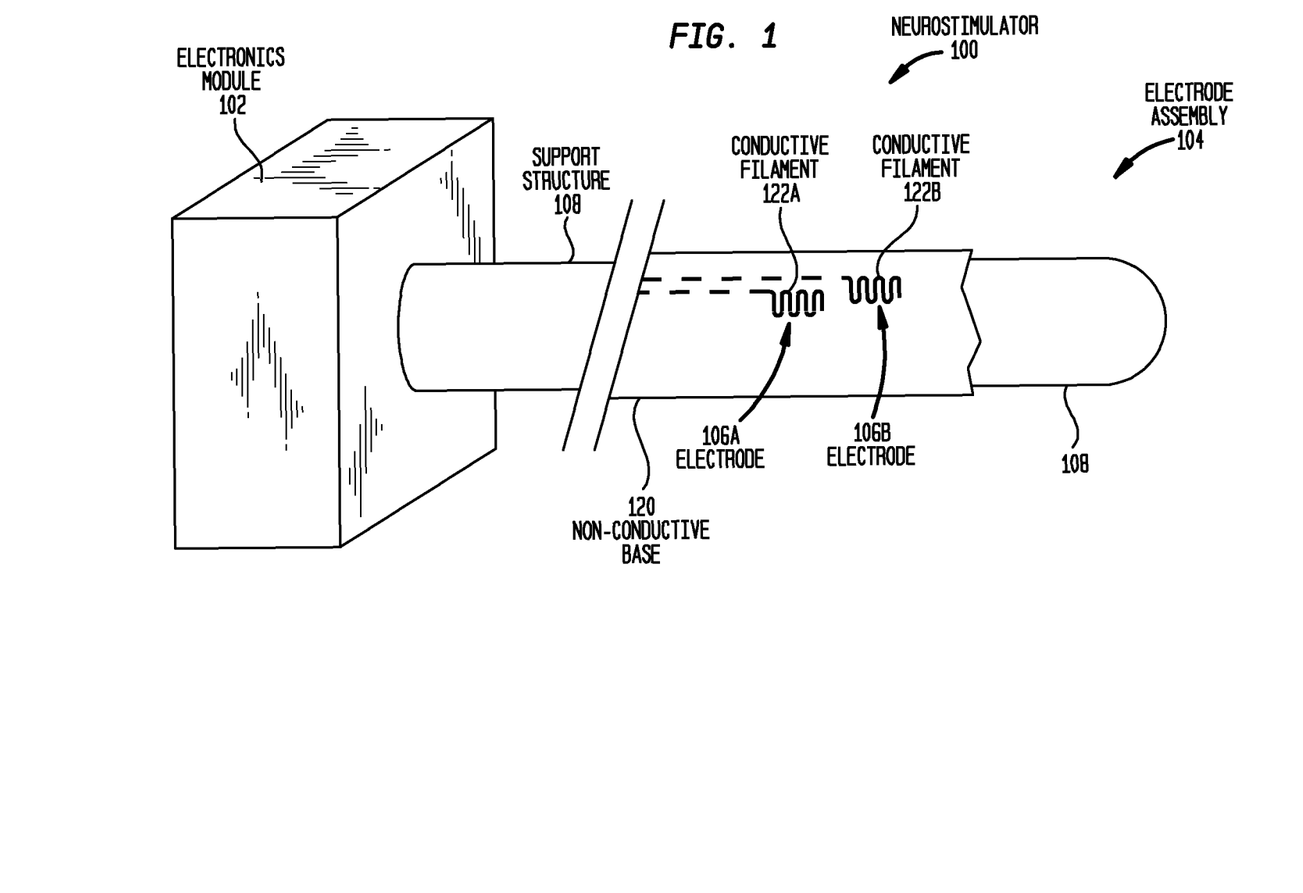
FIG. 1 is a perspective view of an exemplary active implantable medical device (AIMD), namely a neurostimulator, in accordance with embodiments of the present invention.

FIG. 1 is a perspective view of an active implantable medical device (AIMD), namely a neurostimulator 100, in accordance with embodiments of the present invention. Neurostimulator 100 comprises an implantable, hermetically sealed electronics module 102, and a tissue interface, shown as electrode assembly 104. In the illustrative embodiments of FIG. 1, electrode assembly 104 comprises a biocompatible, electrically non-conductive support structure 108 mechanically coupled to electronics module 102. Disposed on the surface of support structure 108 is a biocompatible, electrically non-conductive needle-piercable base 120. Two electrodes 106 are stitched into base 120 using biocompatible electrically conductive filaments 122. Conductive filaments 122 extend to electronics module 102. Needle-piercable bases and the stitching of conductive filaments thereto are described in greater detail below.

Figure 2:
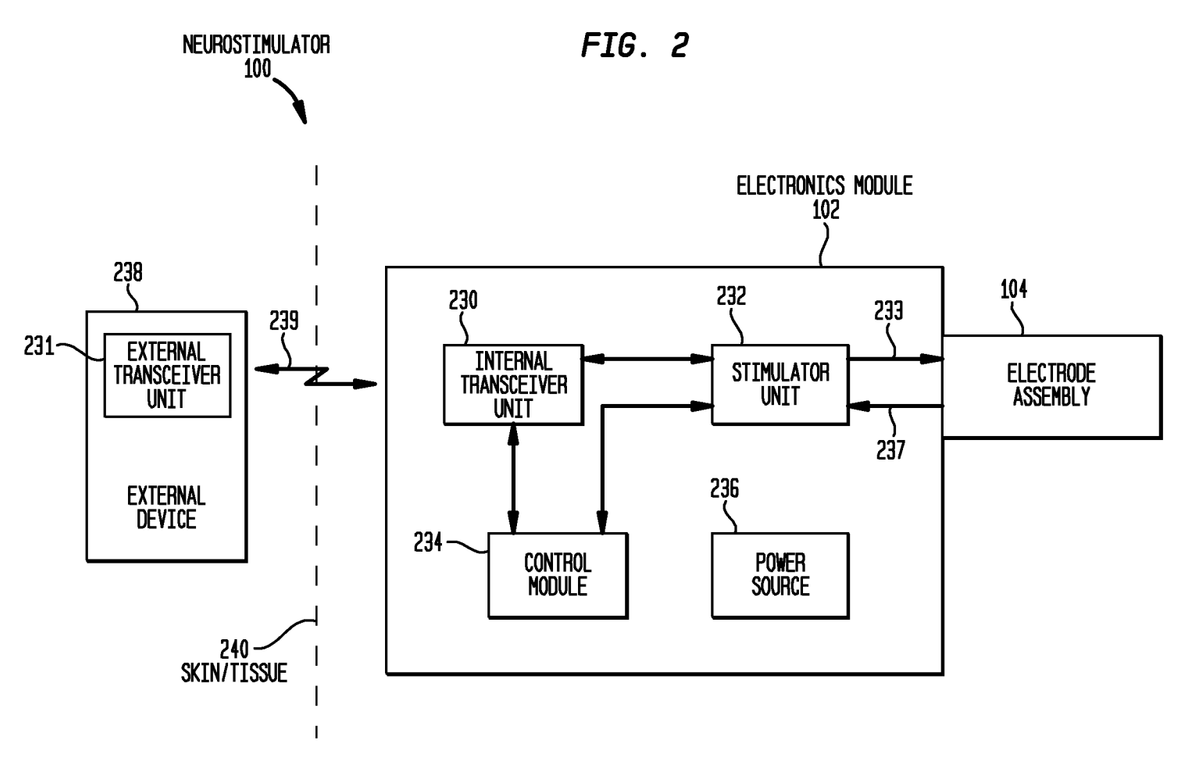
FIG. 2 is a functional block diagram of the neurostimulator illustrated in FIG. 1, in accordance with embodiments of the present invention.

FIG. 2 is a functional block diagram illustrating one exemplary arrangement of electronics module 102 of neurostimulator 100 of the present invention. In the embodiments of FIG. 2, electronics module 102 is implanted under a patient's skin/tissue 240, and cooperates with an external device 238. External device 238 comprises an external transceiver unit 231 that forms a bi-directional transcutaneous communication link 239 with an internal transceiver unit 230 of electronics module 102. Transcutaneous communication link 239 may be used by external device 238 to transmit power and/or data to electronics module 102. Similarly, transcutaneous communication link 239 may be used by electronics module 102 to transmit data to external device 238.

As used herein, transceiver units 230 and 231 each include a collection of one or more components configured to receive and/or transfer power and/or data. Transceiver units 230 and 231 may each comprise, for example, a coil for a magnetic inductive arrangement, a capacitive plate, or any other suitable arrangement. As such, in embodiments of the present invention, various types of transcutaneous communication, such as infrared (IR), electromagnetic, capacitive and inductive transfer, may be used to transfer the power and/or data between external device 238 and electronics module 102.

In the specific embodiment of FIG. 2, electronics module 102 further includes a stimulator unit 232 that generates electrical stimulation signals 233. Electrical stimulation signals 233 are delivered to a patient's tissue via electrodes 106 (FIG. 1) of electrode assembly 104. Stimulator unit 232 may generate electrical stimulation signals 233 based on, for example, data received from external device 238, signals received from a control module 234, in a pre-determined or pre-programmed pattern, etc.

As noted above, in certain embodiments, electrodes 106 of electrode assembly 104 are configured to record or monitor the physiological response of a patient's tissue. In such embodiments, signals 237 representing the recorded response may be provided to stimulator unit 232 for forwarding to control module 234, or to external device 238 via transcutaneous communication link 239.

In the embodiments of FIG. 2, neurostimulator 100 is a totally implantable medical device that is capable of operating, at least for a period of time, without the need for external device 238. Therefore, electronics module 102 further comprises a rechargeable power source 236 that stores power received from external device 238. The power source may comprise, for example, a rechargeable battery. During operation of neurostimulator 100, the power stored by the power source is distributed to the various other components of electronics module 102 as needed. For ease of illustration, electrical connections between power source 236 and the other components of electronics module 102 have been omitted. FIG. 2 illustrates power source 236 located in electronics module 102, but in other embodiments the power source may be disposed in a separate implanted location.

Although FIG. 2 illustrates embodiments having an implanted power source, it would be appreciated that, in certain embodiments, the implanted power source may be omitted. For example, neurostimulator 100 may be configured to operate based on power continually or periodically provided by an inductive link. In one such embodiment, an external charging device is configured such that when neurostimulator 100 is brought into proximity thereto, the charging device continually or periodically provides power to the neurostimulator.

FIG. 2 illustrates specific embodiments of the present invention in which neurostimulator 100 cooperates with an external device 238. It should be appreciated that in alternative embodiments, deep brain stimulation 100 may be configured to operate entirely without the assistance of an external device.

Figure 3A:
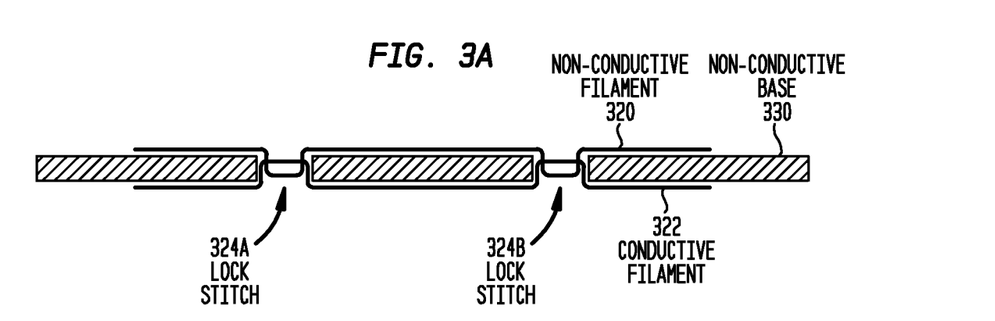
FIG. 3A is a cross-sectional view of a non-conductive base having a conductive filament sewn therein, in accordance with embodiments of the present invention.
Figure 3B:
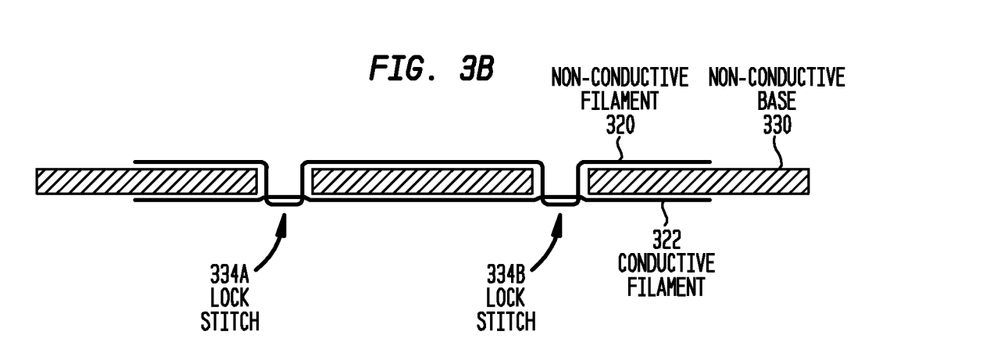
FIG. 3B is a cross-sectional view of a non-conductive base having a conductive filament sewn therein, in accordance with embodiments of the present invention.

As noted above, embodiments of the present invention are generally directed to an AIMD in which at least one of the electronics module and the tissue interface comprises an electrically non-conductive, biocompatible and needle-piercable base. One or more biocompatible electrically conductive filaments are stitched to the base. As used herein, stitching a conductive filament to a base refers to sewing, embroidering or otherwise securing the filament to the base through the use of hand or machine needlework. As such, lock stitches, chain stitches, running stitches, overlocks, coverstitches, couching, etc. may be used to secure the conductive filament to the base. The conductive filament may be sewn into the base through the use of one or more electrically non-conductive filaments, or conductive filament may be directly sewn into the base (i.e. without the use of a supporting non-conductive filament to secure the conductive filament). FIGS. 3A and 3B illustrate embodiments of the present invention in which a conductive filament is secured to a base using lock stitches.

FIG. 3A is a side view of a base 330 in accordance with embodiments of the present invention. As noted, base 330 is electrically non-conductive and biocompatible. To permit the use of needlework to secure a conductive filament to the base, base 330 is also needle-piercable. That is, base 330 is configured such that it may be repeatedly penetrated by a sewing or embroidering needle without experiencing significant structural damage. Base 330 may comprise, for example, woven or continuous fabric, a solid sheet or film of synthetic material, etc.

In certain embodiments, base 330 comprises a solid sheet or film of thermo-plastic material. In such embodiments, a heated needle is used to stitch a conductive filament into base 330 so that the material around each perforation will melt and re-seal after the stitch is formed. The re-sealing of base 300 secures the conductive filament to the base, thereby increasing reliability. Such embodiments also have the advantage that thermo-plastic base 330 may be molded into a desired shape before or after stitching the conductive filament thereto.

As noted, in the embodiments of FIG. 3A, a conductive filament is sewn to base 330 using a plurality of lock stitches 324. Lock stitches 324 are formed through the use of two filaments referred to as a needle filament 320 and a bobbin filament 322. Needle filament 320 comprises an electrically non-conductive strand of yarn, wire, thread, polymer fiber or filament, referred to as non-conductive filament 320 herein. Bobbin filament 322 comprises an electrically conductive strand of yarn, wire, thread, metal coated fiber or metal filament, generally referred to as conductive filament 322 herein.

In the embodiments of FIG. 3A, non-conductive filament 320 and conductive filament 322 are disposed on opposing sides of base 330. During the formation of lock stitches 324, non-conductive filament is carried through base 330 by a needle, thereby forming a loop of non-conductive filament on the conductive filament side of the base. Conductive filament 322 is wound around a bobbin (not shown), and a circular hook mechanism (not shown) is disposed concentrically about a section of the bobbin. Bobbins and circular hook mechanisms are well known in the art. To form a lock stitch 324, the circular hook mechanism rotates around the bobbin in a manner that causes the hook to pick up the loop of non-conductive filament 320. The circular hook mechanism carries the loop around the outside of the bobbin, thereby capturing conductive filament 322 inside needle filament 320. The needle is then withdrawn back through base 330, pulling conductive filament 322 close to the base. This process is repeated for each stitch 324.

FIG. 3A illustrates lock stitches 324 that are arranged such that non-conductive filament 320 and conductive filament 322 cross over in the center of base 330. Such stitches are referred to herein as traditional lock stitches. FIG. 3B illustrates an alternative embodiment of the present invention in which lock stitches 334 are formed in substantially the same manner as described above with reference to FIG. 3A. However, in the embodiments of FIG. 3B, the tension of non-conductive filament 320 is altered during the sewing process so that non-conductive filament 320 and conductive filament 322 cross over on the conductive filament side of base 330. Such stitches are referred to herein as modified lock stitches 334.

In the embodiments of FIG. 3B, non-conductive filament 320 retains conductive filament 322 along the surface of base 330. Because conductive filament 322 is not drawn into the center of base 330, the use of modified lock stitches 334 shown in FIG. 3B reduce the bending forces placed on conductive filament 322.

In accordance with embodiments of the present invention, conductive filament 322 is a fine biocompatible wire such as platinum, and non-conductive filament 320 is a resiliently flexible compliant biocompatible, non-conductive thread such as poly-propylene. In certain embodiments, non-conductive filament 320 is an elastomeric thread. It should be appreciated that conductive filament 322 may be less flexible than non-conductive filament 320 because conductive filament 322 is not required to bend as much as non-conductive filament 320.

It should be appreciated that the embodiments of FIG. 3B in which a lock stitch is modified to retain conductive filament 322 entirely on one side of base 330 may also be implemented with other stitch types. For example, certain two-filament chain stitches, overlocks, coverstitches, etc. may be modified to retain conductive filament 322 entirely on one side of base 330.

As noted above, a conductive filament in accordance with embodiments of the present invention may comprise any electrically conductive strand of yarn, wire, thread, metal coated fiber or metal filament. In one embodiment, conductive filament 322 is a fiber manufactured from carbon nanotubes. Alternatively, conductive filament 322 is a platinum or other biocompatible conductive wire. Such wires may be given suitable surface treatments to increase their surface area (e.g. forming a layer of iridium oxide on the surface of platinum, utilizing platinum "blacking," or coating the wire with carbon nanotubes). In other embodiments, the conductive filament comprises several grouped strands of a conductive material, or a polymer coated with a conductive material. In still further embodiments, exemplary filaments are made from multiple strands of similar or dissimilar fibers. In specific such embodiments, at least some strands are conductive (e.g. a hybrid poly-filament of platinum wire and polymer fibers).

It should be appreciated that other types of conductive filaments may also be used.

Also as noted above, a non-conductive filament in accordance with embodiments of the present invention may comprise any non-conductive strand of yarn, wire, thread, polymer fiber or filament. In one embodiment, the non-conductive filament is a biocompatible non-elastomeric polymer material. In another embodiment, the non-conductive filament is a biocompatible elastomeric material. For example, the elastomeric material may comprise, for example, silicone, or silicone polymers. It should be appreciated that other types of non-conductive filaments may also be used.

As noted above, conductive filaments stitched to a base in embodiments of the present invention may perform various functions. For instance, as described below, a conductive filament may be used to form an electrical connection between implanted components, as a component of an antenna, as an electrode, as a component fastening system, etc. FIG. 4A-4D illustrate specific embodiments of the present invention in which a conductive filament is sewn into a base in a pattern that is usable as an electrode of an AIMD. As noted above, an electrode of an AIMD is used to transmit, send or otherwise deliver electrical stimulation signals to, or receive signals from, the tissue of a patient.

For ease of illustration, FIGS. 4A-4D will refer to a conductive filament 322, a non-conductive filament 320, and a base 330 that are substantially the same as illustrated in FIGS. 3A-3B. The embodiments of FIG. 4A-4D are further shown using lock stitches, but it should be appreciated other types of needlework may also be implemented.

In the embodiments of FIGS. 4A-4D, electrodes are formed by stitching conductive filament 322 to non-conductive base 330 in a desired geometric pattern. As shown, electrodes of various geometries and textures may be formed using the embodiments of this invention. For example, in certain embodiments, a shape of an electrode is selected to, for example, maximize surface area for a particular implant location. As such, it should be appreciated that the electrodes shown in FIGS. 4A-4D are merely illustrative.

Figure 4A:
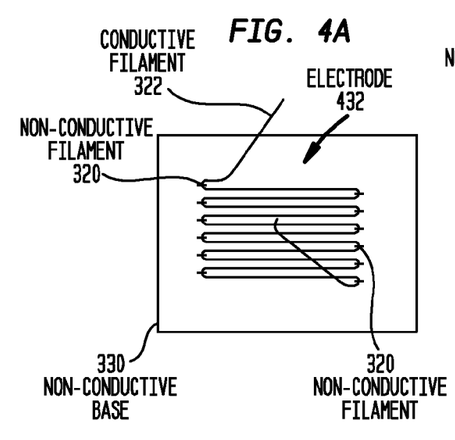
FIG. 4A is a top view of a sewn electrode in accordance with embodiments of a present invention.

A first shape is illustrated in FIG. 4A in which a rectangular electrode 432 is formed. In these embodiments, conductive filament 322 is sewn into a series of parallel rows (stitches), referred to as satin stitch, in which each row has approximately the same length. A non-conductive filament 320 secures conductive filament 322 to the surface of base 330 at the ends of each row For ease of illustration, FIG. 4A illustrates embodiments in gaps are disposed between adjacent stitches. In alternative embodiments, a series of parallel stitches of length/are placed side by side, with no gap between the stitches. In such embodiments, the surface area (sa) of an electrode of length/ and width w may be approximated by Equation (1):

$$sa = \frac{\pi \cdot l \cdot w}{2} \quad \text{Equation (1)}$$

As should be appreciated, gaps between adjacent stitches reduce the surface area of an electrode. However, due to the non-flat profile of a conductive filament, a substantial portion of the filament circumference may make contact with electrolyte solution in patient's body near target tissue to be stimulated. This means that even with some gaps within the electrode, the stimulation surface of the electrode may still be greater than conventional planar electrodes.

In some embodiments, the density of the formed electrode may be varied along its length and/or width. Such embodiments may facilitate field shaping.

Figure 4B:
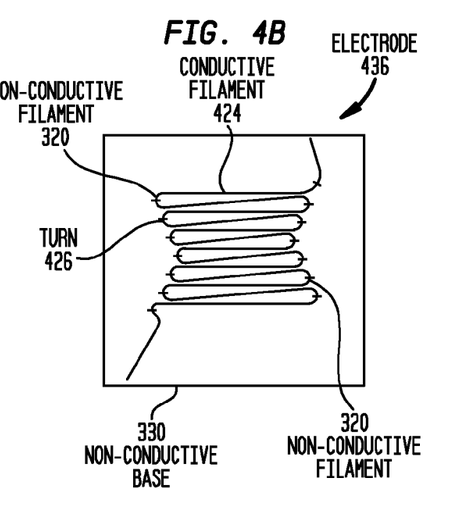
FIG. 4B is a top view of a sewn electrode in accordance with embodiments of a present invention.

FIG. 4B illustrates an electrode 436 that is similar to the embodiments of FIG. 4A. Electrode 436 comprises a series of adjacent stitches of conductive filament 424 secured to base 330 by non-conductive filament 320. Conductive filament 424 is substantially the same as conductive filament 322, except that filament 424 has a larger bend radius than filament 322. As such, electrode 346 is shaped to accommodate this larger bend radius. As shown, the radius of each curve or turn 426 of conductive filament 424 is selected so that conductive filament 424 is not damaged during the sewing process.

Figure 4C:
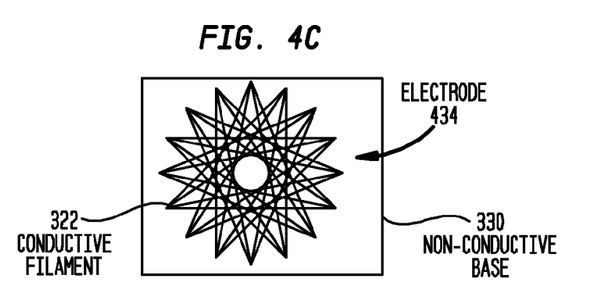
FIG. 4C is a top view of a sewn electrode in accordance with embodiments of a present invention.
Figure 4D:
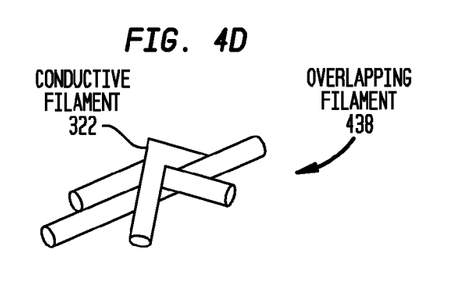
FIG. 4D is a perspective view of a section of an electrode having overlapping layers of filament, in accordance with embodiments of the present invention.

FIG. 4C illustrates another shape for an electrode in accordance with embodiments of the present invention. As shown, conductive filament 322 is stitched to base 330 to form a star shaped electrode 434. In the embodiments of FIG. 4C, during the formation of electrode 434, stitches of conductive filament 322 will overlap with one another. An overlapping section of filament 438 is shown in FIG. 4D. The overlapping filament increases the surface area of the electrode.

As previously noted, a variety of conductive filaments may be used in embodiments of the present invention. In certain embodiments of FIGS. 4A-4D, the conductive filament comprises an insulator coated conductive filament such as, for example, parylene coated platinum wire. In such embodiments, the insulating material is removed from the section of the conductive filament which forms the electrode.

FIGS. 4A-4D illustrate the formation of a single electrode. It should be appreciated that a plurality of electrodes may be formed into a single base 330 to form an electrode assembly, such as shown in FIG. 1. In certain such embodiments, non-conductive base 330 may be formed as a tube or pocket having a plurality of electrodes thereon. The tube may then be fitted on a support structure which is formed from a suitable bio-compatible material. Such a structure may be used to provide mechanical strength and/or form base 330 into a desired shape. This process may be further facilitated if the underlying fabric has elastomeric properties. As noted above, FIG. 1 illustrates a non-conductive tube disposed over a support structure.

Figure 5:
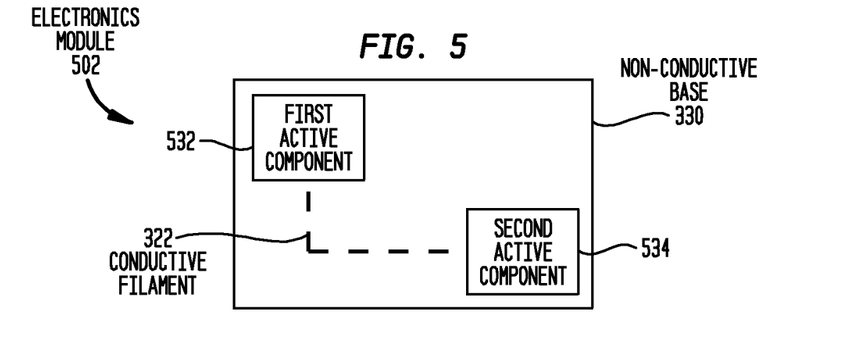
FIG. 5 is top view of an electronics module having first and second components electrically connected by a sewn conductive filament.

FIG. 5 illustrates another embodiment of the present invention in which a conductive filament is used to electrically connect components of an AIMD. For ease of illustration, FIG. 5 refers to a conductive filament 322, a non-conductive filament (not shown) and a base 330 that are substantially the same as illustrated in FIGS. 3A-3B.

Figure 13:
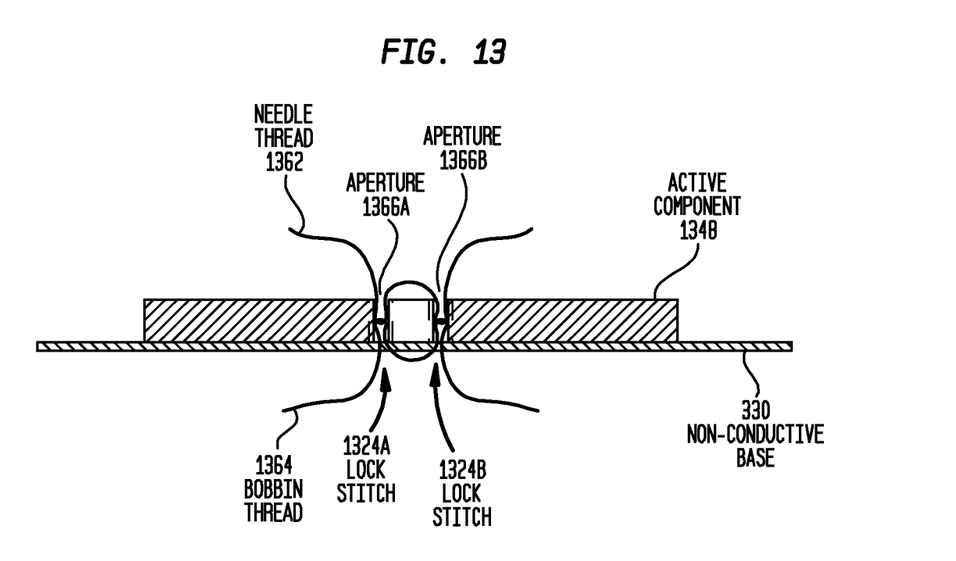
FIG. 13 is a cross-sectional view of an active component sewn to a base in accordance with embodiments of the present invention.

As shown in FIG. 5, first and second active components 532, 534, are attached to non-conductive base 330. FIG. 13 illustrates an exemplary method for attaching components 532 and 534 to base 330. A conductive pathway is stitched into base 330 using conductive filament 322 to electrically connect active components 532, 534. In the illustrative embodiments of FIG. 5, base 330, components 532 and 534 and stitched conductive filament 332 are collectively referred to as electronics module 502.

As used herein, an active component refers to any component that utilizes, or operates with, electrical signals. For example, an active component comprises a stimulator unit, transceiver, power source, control module or other component used in an electronics module of an AIMD. In other embodiments, the active component comprises a low power linear motor. Such an actuator is anchored at a suitable location in the structure and may allow the structure to change shape, for example by providing pressure to an organ or body tissue for therapeutic benefit. In still other embodiments, one of the active components may comprise a component of a drug delivery system, sensor, electrode, etc.

Figure 6:
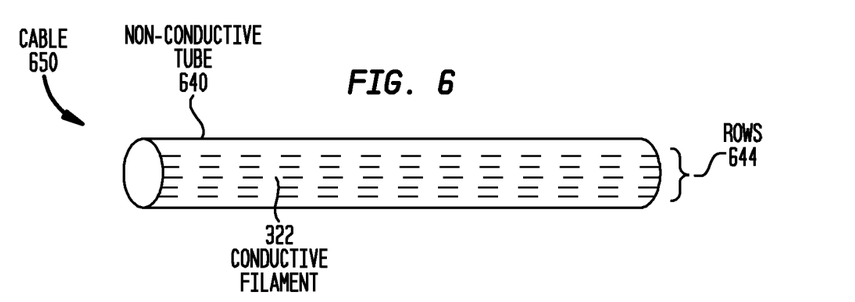
FIG. 6 is a perspective view of cable manufactured in accordance with embodiments of the present invention.

FIG. 6 illustrates a further embodiment of the present invention in which a conductive filament is used to form a multi-core cable 650. In these embodiments, an elongate non-conductive base 640 is provided. As shown in FIG. 6, base 640 has a tubular shape and is referred to as non-conductive tube 640. Several rows 644 of conductive filament 322 are stitched into non-conductive tube 640 to provide a plurality of conductive pathways extending the length of the tube. Cable 650 may be used similar to conventional multi-core cables to electrically connect first and second devices.

Figure 7:
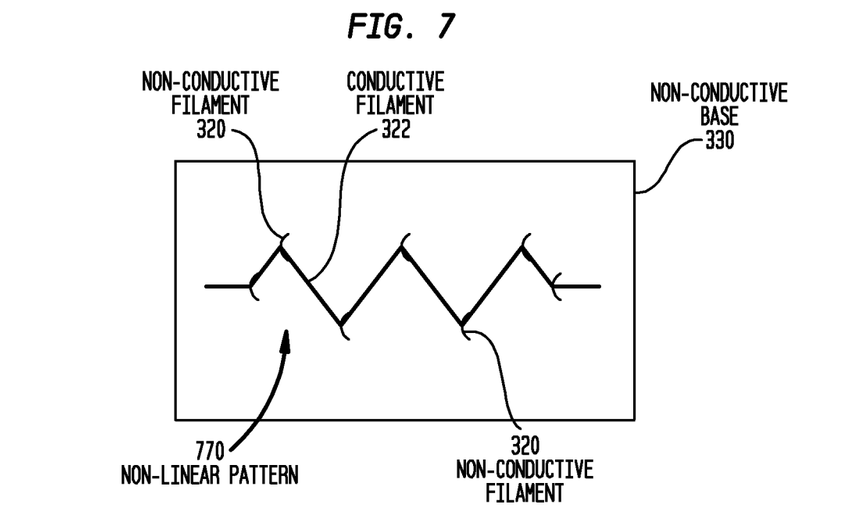
FIG. 7 is a top view of a non-linear pattern of a conductive filament in accordance with embodiments of the present invention.

In certain embodiments of FIGS. 5 and 6, non-conductive bases 530, 640, may be elastomeric so as to facilitate stretching of the base. In such embodiments, in order to prevent damage to the conductive pathways formed by conductive filaments 322, the conductive filament may follow a non-linear pattern 770, such as, for example, the zig-zag pattern 770 shown in FIG. 7. The non-linear pattern allows extension of conductive filament 322 upon stretching of base 330 without damaging the structural integrity of the conductive filament.

Figure 8:
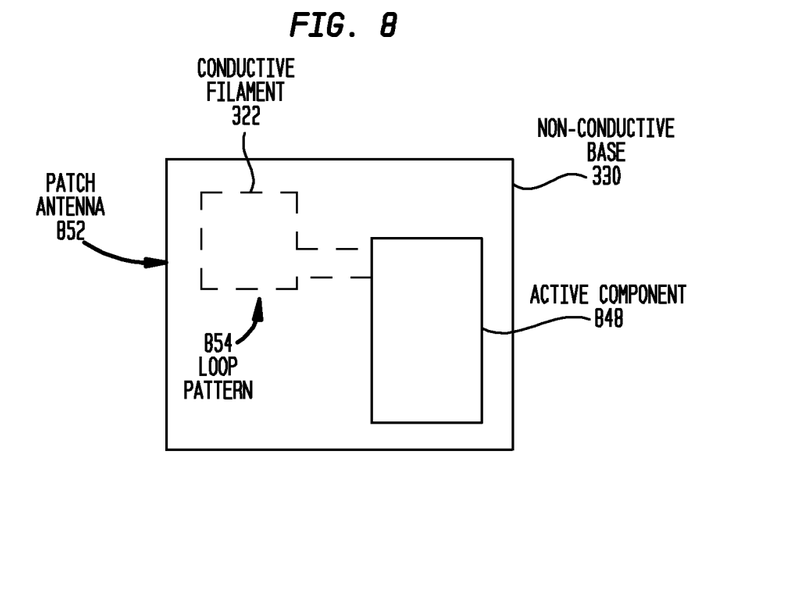
FIG. 8 is a top view of a patch antenna in accordance with embodiments of the present invention.

As noted above, in embodiments of the present invention, a conductive filament is stitched to a base in a pattern that is usable by an active component to at least one of transmit or receive signals. FIGS. 4A-4D illustrate exemplary such embodiments in which a conductive filament is stitched in a pattern to transmit or deliver electrical signals to, or receive signals from, a patient's tissue. FIG. 8 illustrates an alternative such embodiment. For ease of illustration, FIG. 8 refers to a conductive filament 322 and a base 330 that are substantially the same as illustrated in FIGS. 3A-3B.

In the embodiments of FIG. 8, an active component 848 is attached to non-conductive base 330. Active component 848 comprises one or more antenna elements, and conductive filament 322 is stitched into base 300 in a pattern that is usable by active component 848 to transmit or receive electromagnetic waves. That is, active component 848 and conductive filament 322 collectively form an antenna, referred to as patch antenna 852 in the specific embodiments of FIG. 8. In the embodiments of FIG. 8, conductive filament is stitched in a loop pattern 854.

Although FIG. 8 illustrates a specific patch antenna 852, it should be appreciated that other transmitting/receiving devices may be formed using embodiments of the present invention. For example, in certain embodiments the conductive filament is sewn into a tight bundle to form a coil for a transcutaneous energy transfer (TET) system.

Figure 9:
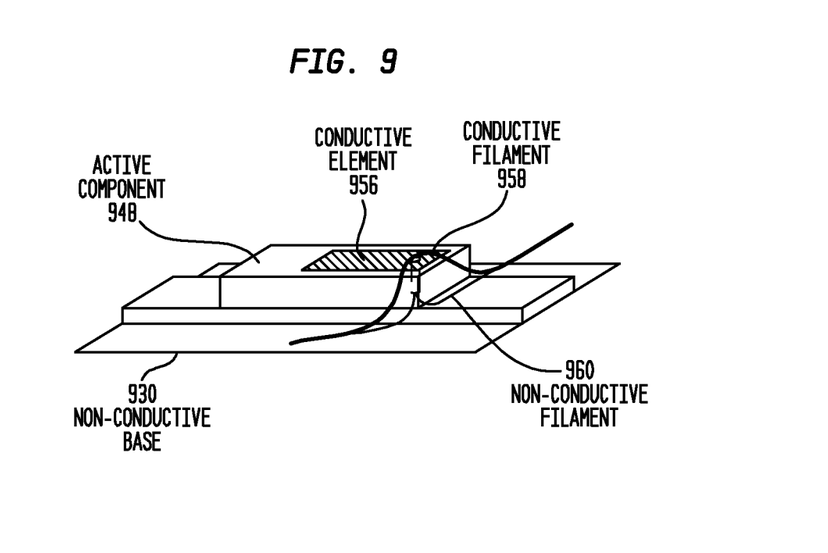
FIG. 9 is a perspective view of a termination device in accordance with embodiments of the present invention.

FIG. 9 illustrates a still other embodiment of the present invention. In the embodiments of FIG. 9, an active component 948 is attached to a non-conductive base 930. Disposed on active component 948 is a conductive element 956. In these embodiments, a termination device is fabricated by using non-conductive filament 960 to pull conductive filament 958 onto conductive element 956.

Figure 10:
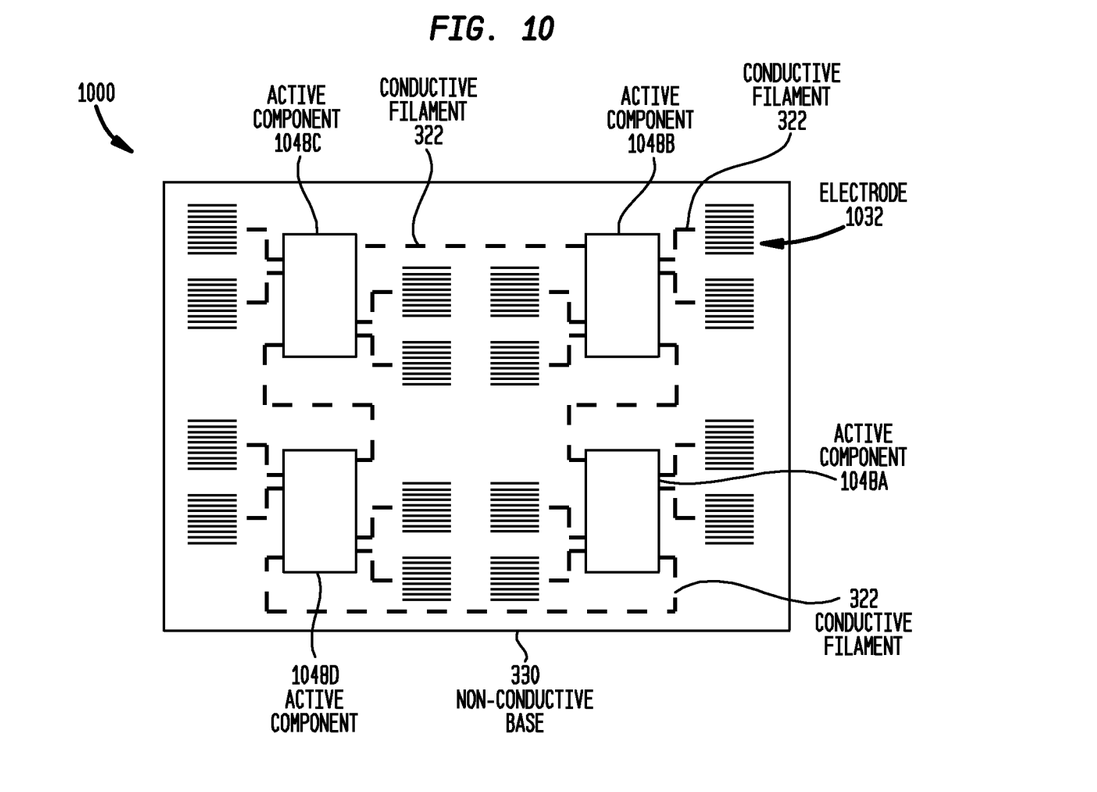
FIG. 10 is a top view of an implantable system in accordance with embodiments of the present invention.

FIGS. 4A-9 described above illustrate embodiments of the present invention in which a conductive filament is stitched to a non-conductive base to form various structures. FIG. 10 is a schematic diagram of a system 1000 formed using one or more of the above described embodiments. For ease of illustration, FIG. 10 refers to conductive filaments 322 and a base 330 that are substantially the same as described above with reference to FIGS. 3A-3B.

As shown in FIG. 10, system 1000 comprises a plurality of active components 1048. The components are electrically connected to one another by conductive filaments 322 as described above with reference to FIG. 5. Furthermore, a plurality of rectangular electrodes 1032 are formed as described above with reference to FIG. 4A.

In embodiments of FIG. 10, system 1000 is referred to as an intelligent implantable substrate. In specific such embodiments, non-conductive base 330 comprises a fabric, and system 1000 is referred to as an intelligent implantable fabric.

Figure 11:
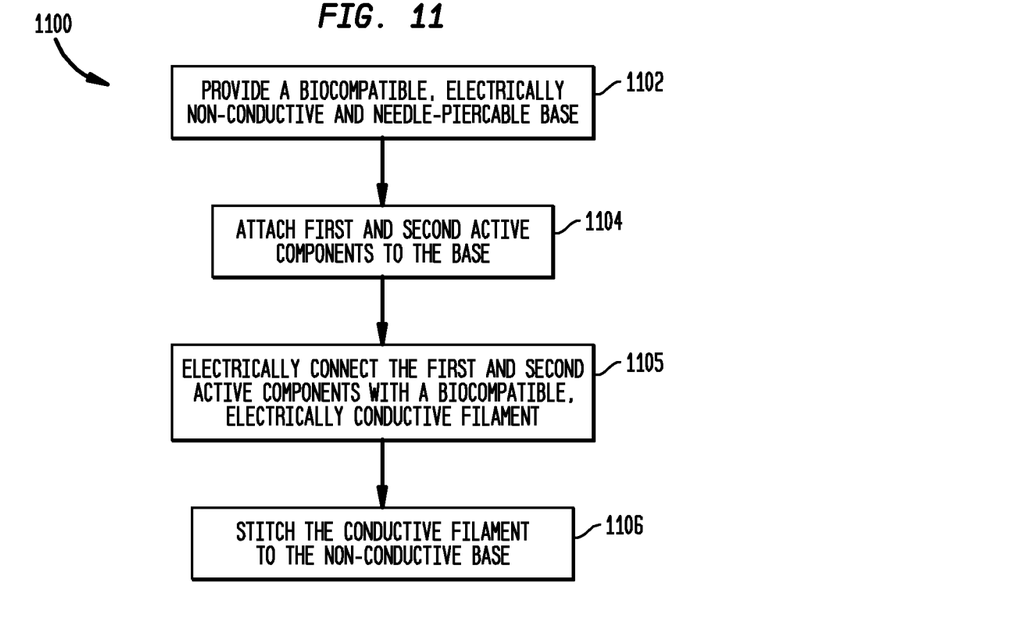
FIG. 11 is a high level flowchart illustrating a method for manufacturing components of an AIMD in accordance with embodiments of the present invention.

FIG. 11 is a high level flowchart illustrating a method 1100 for manufacturing an electronics module of an active implantable medical device (AIMD) in accordance with embodiments of the present invention. Method 1100 begins at block 1102 where a biocompatible, electrically non-conductive and needle-piercable base is provided. At block 1104, first and second active components are attached to the non-conductive base. The active components may be attached to the base as described below with reference to FIG. 13. At block 1105, the first and second components are electrically connected with a biocompatible, electrically conductive filament. At block 1106, the electrically conductive filament is stitched to the base.

Figure 12A:
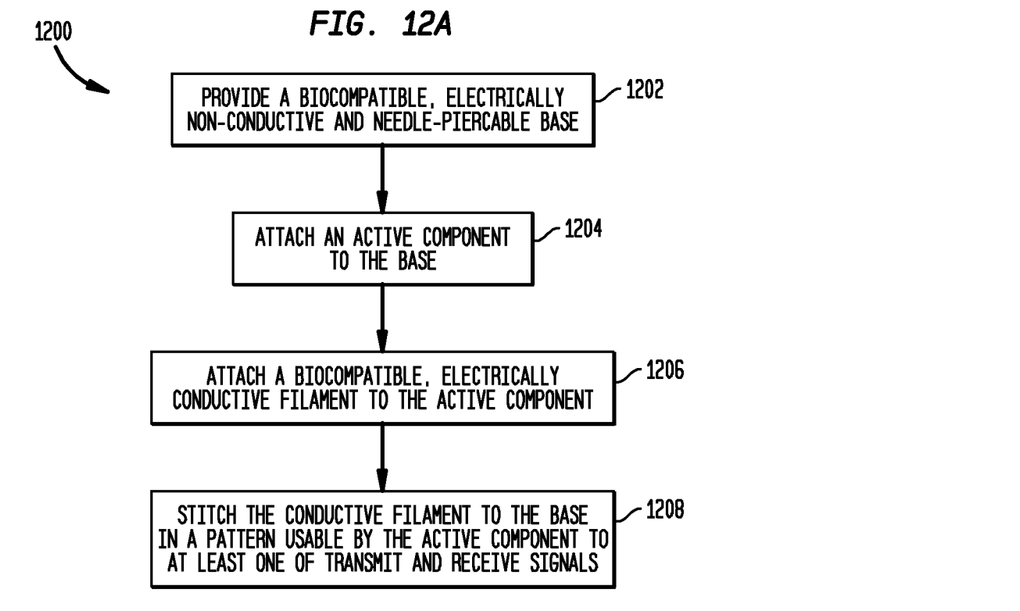
FIG. 12A is a high level flowchart illustrating a method for manufacturing components of an AIMD in accordance with embodiments of the present invention.

FIG. 12A is a high level flowchart illustrating a method 1200 for manufacturing a system of an active implantable medical device (AIMD) in accordance with embodiments of the present invention. Method 1200 begins at block 1202 where a biocompatible, electrically non-conductive and needle-piercable base is provided. At block 1204, an active component is attached to the non-conductive base. The active component may be attached to the base as described below with reference to FIG. 13. At block 1206, a biocompatible electrically conductive filament is attached to the active component. The conductive filament is stitched to the base at block 1208 in a pattern usable by the active component to at least one of transmit and receive signals.

Figure 12B:
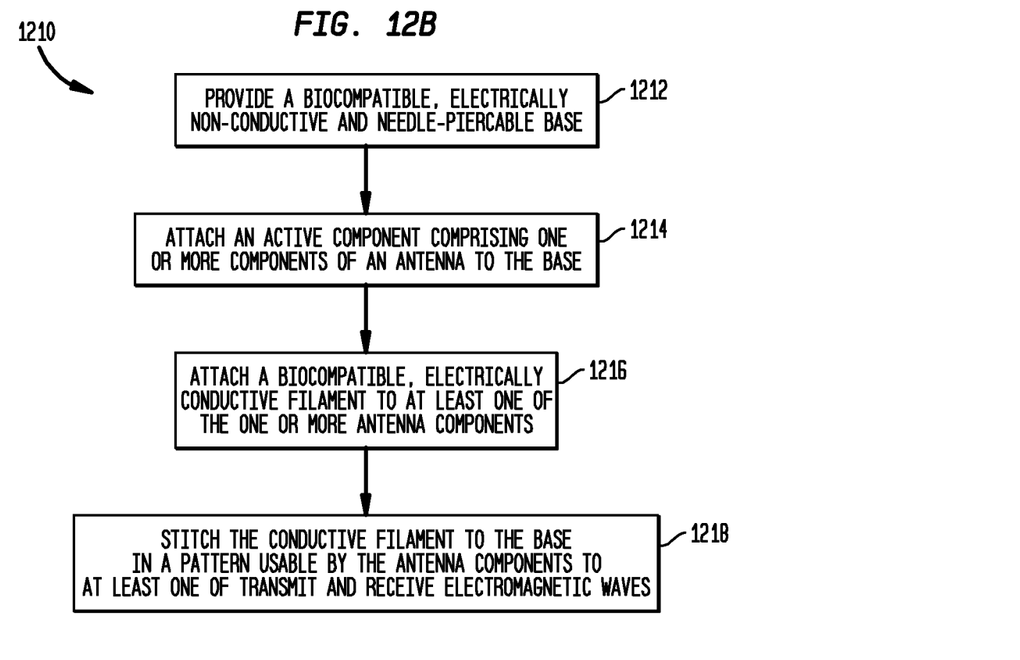
FIG. 12B is a flowchart illustrating the operations performed in accordance with one embodiment of FIG. 12A.

FIG. 12B is a flowchart illustrating one variation of method 1200 of FIG. 12A, referred to as method 1210. Method 1210 begins at block 1212 where a biocompatible, electrically non-conductive and needle-piercable base is provided. At block 1214, an active component comprising one or more components of an antenna is attached to the non-conductive base. The active component may be attached to the base as described below with reference to FIG. 13. At block 1216, a biocompatible electrically conductive filament is attached to at least one of the antenna components. The conductive filament is stitched to the base at block 1218 in a pattern usable by the antenna components to at least one of transmit and receive electromagnetic waves.

Figure 12C:
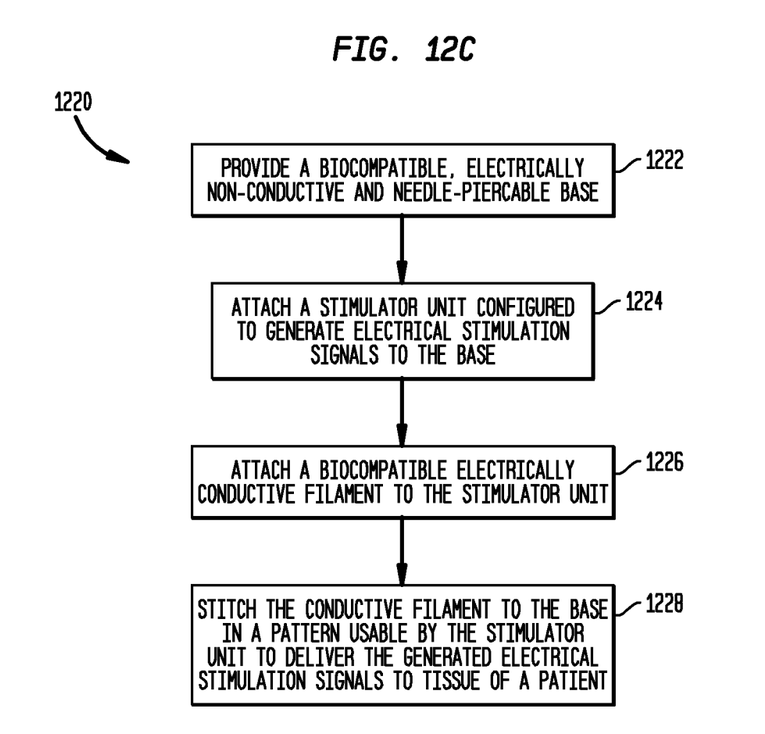
FIG. 12C is a flowchart illustrating the operations performed in accordance with one embodiment of FIG. 12A.

FIG. 12C is a flowchart illustrating another variation of method 1200 of FIG. 12A, referred to as method 1220. Method 1220 begins at block 1222 where a biocompatible, electrically non-conductive and needle-piercable base is provided. At block 1224, a stimulator unit configured to generate electrical stimulation signals is attached to the non-conductive base. The stimulator unit may be attached to the base as described below with reference to FIG. 13. At block 1226, a biocompatible, electrically conductive filament is attached to the stimulator unit. The conductive filament is stitched to the base at block 1228 in a pattern usable by the stimulator unit to deliver the generated electrical stimulation signals to tissue of a patient.

As noted above, embodiments of the present invention may include one or more components attached to a non-conductive base. As would be appreciated, several methods including adhesive, sewing, etc., may be implemented for attaching a component to a base. FIG. 13 is a cross-sectional view of a component sewn to a base in accordance with embodiments of the present invention.

As shown in FIG. 13, an active component 1348 has apertures 1366 extending there through. A lock stitch 1324 is formed in each aperture 1366 using a needle thread 1362 and bobbin thread 1364, as described above with reference to FIGS. 3A and 3B. Threads 1362, 1364 may each comprise a conductive or non-conductive filament. It should be appreciated that any type of needlework may be used to secure a component to base 330, and lock stitches 1324 are merely illustrative.

Figure 14A:
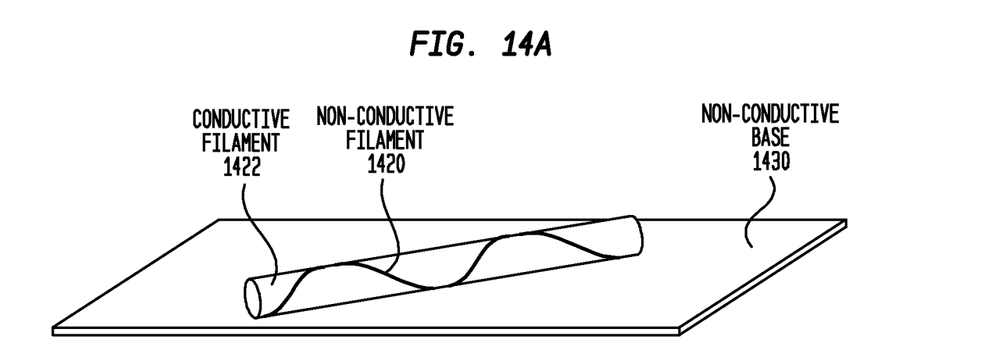
FIG. 14A is perspective view of a conductive filament stitched to a base in accordance with embodiments of the present invention.
Figure 14B:
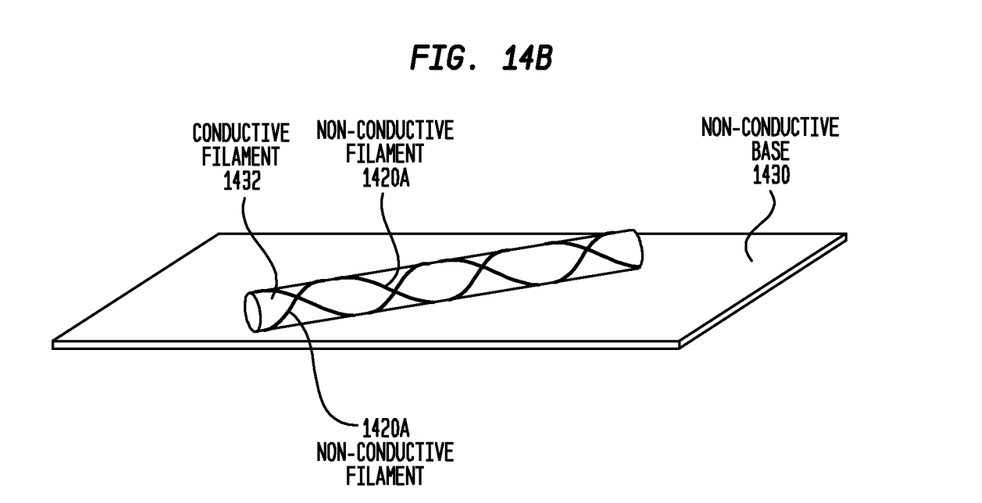
FIG. 14B is perspective view of a conductive filament stitched to a base in accordance with embodiments of the present invention.

FIGS. 14A and 14B illustrate an alternative method for stitching a conductive filament 1422 to a non-conductive base 1430 in accordance with embodiments of the present invention. In these embodiments, conductive filament 1422 is not used to form part of the stitch. Rather, one or more non-conductive filaments 1420 are stitched over conductive filament 1420 in, for example, a zig-zag pattern to secure the conductive filament to non-conductive base 1430. FIG. 14A illustrates embodiments in which one non-conductive filament 1420 is used to secure conductive filament 1422, while FIG. 14B illustrates embodiments in which two non-conductive filaments 1420 are used. In specific embodiments of FIG. 14B, a lock stitch may be formed from two non-conductive filaments.

It should be appreciated that variations of the above described embodiments are within the scope of the present invention. For example, in certain embodiments, the non-conductive base, or the non-conductive filament may comprise a drug-eluting polymer. In such embodiments, drugs or other therapeutic agents may be incorporated into the structure and may be automatically dispensed once the AIMD has been implanted.

As noted above, in certain embodiments an elastomeric material may be used as a non-conductive filament and/or the non-conductive base. In embodiments in which an elastomeric material is used as the non-conductive filament, the filament may be stretched as it sewn so that the filament will contract after the sewing process. This may help to form the base or the stitches into a desired shape.

In yet another embodiment of the present invention, an element of an AIMD may be formed by sewing a memory metal thread such as nitinol, insulated as required, into a non-conductive base. In such embodiments, the memory metal is preformed into a first shape, and is configured to adopt a second shape during or following implantable of the AIMD into the patient.

In a still other embodiment of the present invention, one or more secondary non-conductive threads may be incorporated into a section of the base. These threads may be used to manipulate the shape of the structure through the application of appropriate tension to the secondary threads. Furthermore, in embodiments of the present invention a conductive thread which is suitable for strain gauge applications may be sewn into one or more appropriate parts of a base so that the strain across a section of the base may be measured.

The present application is related to commonly owned and co-pending U.S. Utility patent applications entitled "Knitted Electrode Assembly For An Active Implantable Medical Device," filed Aug. 28, 2009, "Knitted Electrode Assembly And Integrated Connector For An Active Implantable Medical Device," filed Aug. 28, 2009, "Knitted Catheter," filed Aug. 28, 2009, "Bonded Hermetic Feed Through For An Active Implantable Medical Device," filed Aug. 28, 2009, and "Electronics Package For An Active Implantable Medical Device," filed Aug. 28, 2009. The contents of these applications are hereby incorporated by reference herein.

While various embodiments of the present invention have been described above, it should be understood that they have been presented by way of example only, and not limitation. It will be apparent to persons skilled in the relevant art that various changes in form and detail may be made therein without departing from the spirit and scope of the invention. Thus, the breadth and scope of the present invention should not be limited by any of the above-described exemplary embodiments, but should be defined only in accordance with the following claims and their equivalents. All patents and publications discussed herein are incorporated in their entirety by reference thereto.

What is claimed is:

1. A method of manufacturing an active implantable medical device (AIMD), comprising:
    providing a biocompatible, electrically non-conductive and needle-pierce-able base;
    stitching a repeating pattern with a biocompatible, electrically conductive filament to the non-conductive base;
    stitching at least one active component of an electronics module to the non-conductive base; and
    attaching, with the electrically conductive filament, the stitched repeating pattern of the electrically conductive filament to the at least one active component to transmit and/or receive signals,
    wherein the at least one active component includes a stimulator unit configured to generate electrical stimulation, signals and the electrically conductive filament stitched in the repeating pattern delivers the electrical stimulation signals to tissue of a patient.

2. The method of claim 1, wherein stitching the conductive filament to the base comprises:
    securing the conductive filament to the base with a biocompatible, electrically nonconductive filament sewn into the non-conductive base.

3. The method of claim 2, wherein the conductive filament is substantially positioned on a first side of the base, and wherein the non-conductive filament is disposed substantially on an opposing side of the base, and wherein the method further comprises:
    stitching the conductive filament to the non-conductive base by forming a plurality of interacting lock stitches from the non-conductive filament and the conductive filament.

4. The method of claim 3, further comprising:
    forming the stitches such that the conductive filament remains entirely on the first side of the base.

5. The method of claim 1, wherein stitching the conductive filament to the base comprises:
    directly sewing the conductive filament into the base without the use of a non-conductive filament.

6. The method of claim 1, wherein the at least one active component comprises components of an antenna.

7. The method of claim 6, further comprising:
    stitching the conductive filament into a loop pattern.

8. The method of claim 1, wherein the at least one active component comprises a stimulator unit configured to generate electrical stimulation signals, and wherein the method further comprises:
    stitching the conductive filament to the base in a pattern usable by the stimulator unit to deliver the electrical stimulation signals to tissue of a patient.

9. The method of claim 8, further comprising:
    stitching the conductive filament into a series of substantially parallel linear rows.

10. The method of claim 8, further comprising:
    stitching the conductive filament into a plurality of stitches, wherein two or more of the stitches overlap with one another.

11. The method of claim 1, wherein providing an electrically non-conductive, biocompatible and needle-pierce-able base comprises:
    providing a fabric base.

12. The method of claim 1, wherein providing an electrically non-conductive, biocompatible and needle-pierce-able base comprises:
providing a thermo-softening plastic base.

13. The method of claim 12, further comprising:
molding the thermo-softening plastic base into a desired shape.

14. An active implantable medical device (AIMD), comprising:
a biocompatible, electrically non-conductive and needle-pierce-able base;
at least one active component of an electronics module stitched to the non-conductive base;
a biocompatible, electrically conductive filament stitched to the base in a repeating pattern and attached to the at least one active component to transmit and/or receive signals,
wherein the at least one active component includes a stimulator unit configured to generate electrical stimulation signals, and the electrically conductive filament stitched in the repeating pattern delivers the electrical stimulation signals to tissue of a patient.

15. The AIMD of claim 14, further comprising a biocompatible, electrically non-conductive filament sewn with the conductive filament to stitch the conductive filament to the nonconductive base.

16. The AIMD of claim 15, wherein the conductive filament is substantially positioned on a first side of the base, and wherein the non-conductive filament is disposed substantially on an opposing side of the base, and wherein a plurality of interactive lock stitches formed from the conductive filament and the non-conductive filament secure the conductive filament to the base.

17. The AIMD of claim 16, wherein the conductive filament remains entirely on the first side of the base.

18. The AIMD of claim 14, wherein the at least one active component comprises components of an antenna, and wherein the conductive filament is stitched to the base in a pattern usable with the antenna components to transmit and/or receive electromagnetic signals.

19. The AIMD of claim 18, wherein the conductive filament is stitched into the non-conductive base in a loop pattern.

20. The AIMD of claim 14, wherein the at least one active component comprises a stimulator unit configured to generate electrical stimulation signals, and wherein the conductive filament is stitched to the base in a pattern usable by the stimulator unit to deliver the electrical stimulation signals to tissue of a patient.

21. The AIMD of claim 20, wherein the conductive filament is stitched into the non-conductive base in a series of substantially parallel linear rows.

22. The AIMD of claim 20, wherein the conductive filament is stitched into the non-conductive base in a plurality of rows, wherein two or more of the rows overlap with one another.

23. The AIMD of claim 14, wherein the base comprises a fabric.

24. The AIMD of claim 14, wherein the base comprises a thermo-softening plastic material.

25. The AIMD of claim 14, wherein the conductive filament comprises a shape memory material.

* * * * *